United States Patent
Kraus et al.

(10) Patent No.: US 6,767,466 B2
(45) Date of Patent: Jul. 27, 2004

(54) LEUKOCYTE FILTER CONSTRUCTION

(75) Inventors: Menahem Kraus, Rehovot (IL); Yefet Gamlieli, Kiriat Ekron (IL)

(73) Assignee: Teva Medical Ltd., Ashdod (IL)

( * ) Notice: Subject to any disclaimer, the term of this patent is extended or adjusted under 35 U.S.C. 154(b) by 0 days.

(21) Appl. No.: 10/117,324

(22) Filed: Apr. 8, 2002

(65) Prior Publication Data

US 2003/0189003 A1 Oct. 9, 2003

(51) Int. Cl.[7] .......................... B01D 37/00; B01D 29/00
(52) U.S. Cl. ...................... 210/649; 210/483; 210/488; 210/489; 210/505; 435/2
(58) Field of Search ................................ 210/483, 488, 210/489, 496, 500.21, 500.29, 504, 505, 506, 649, 767; 435/2

(56) References Cited

U.S. PATENT DOCUMENTS

| | | | |
|---|---|---|---|
| 4,701,267 A | * 10/1987 | Watanabe et al. | 210/806 |
| 4,925,572 A | 5/1990 | Pall | |
| 4,936,998 A | * 6/1990 | Nishimura et al. | 210/638 |
| 5,362,406 A | * 11/1994 | Gsell et al. | 210/767 |
| 5,707,526 A | 1/1998 | Kraus et al. | |
| 5,820,755 A | 10/1998 | Kraus et al. | |
| 6,168,718 B1 | * 1/2001 | Sutter et al. | 210/651 |
| 6,422,397 B1 | * 7/2002 | Lynn et al. | 210/489 |
| 2001/0037078 A1 | * 11/2001 | Lynn et al. | 604/6.09 |

FOREIGN PATENT DOCUMENTS

| | | |
|---|---|---|
| EP | 155003 | 9/1985 |
| EP | 406485 | 1/1991 |

* cited by examiner

*Primary Examiner*—John Kim
(74) *Attorney, Agent, or Firm*—Eitan, Pearl, Latzer & Cohen Zedek, LLP

(57) ABSTRACT

A filter unit for removing leukocytes from a leukocyte-containing suspension by passing the suspension through a filter unit. The filter unit may comprise a main filter for blocking the leukocytes and a post-filter for preventing leakage of the leukocytes having a higher median pore size than the main filter and placed downstream of the main-filter.

25 Claims, 2 Drawing Sheets

LEUKOCYTE FILTER CONSTRUCTION

FIELD OF THE INVENTION

The invention relates to a method for removing leukocytes from a leukocyte-containing suspension and particularly from blood-derived suspensions. The invention also relates to a filter unit construction which can be used in the above method.

BACKGROUND OF THE INVENTION

Leukocytes in transfused blood are in most cases not only superfluous but often detrimental. Leukocytes in the blood have been found to cause non-hemolytic febrile reactions and alloimmunization as well as to harbor viruses.

Donated blood can be used without prior treatment ("whole blood"), or, more frequently, is processed to produce a red cell or platelet concentrate. Various methods have been developed to remove leukocytes from these blood products, the most popular being filtration methods.

EP 155003 (to Asahi) and U.S. Pat. No. 4,925,572 (to Pall) describe filtration methods using fibrous, non-woven media to capture the leukocytes as the blood suspension is passed through them. A leukocyte removal rate of over 98% can be obtained using these methods. The disadvantage of these methods is that the filter units used in them must be composed of many layers of filter media in order to reduce leukocyte counts efficiently while at the same time providing a reasonable flow rate. This makes industrial assembly cumbersome and expensive.

An alternate method of leukocyte filtration has been described in European Patent Application EP 406485 (to NPBI Netherlands). This method uses continuous porous membranes for the filtration process instead of fibers. Using cellulose acetate, an exemplary material as described in the above application, results in over 35% of leukocytes remaining in the blood filtrate, as can be seen in FIG. 9. Thus, the above method resulted in a leukocyte removal of less than 65% as compared to greater than 98% for conventional methods. The authors of the above application came to the conclusion that a series of stacked membranes having decreasing pore size in the blood flow direction ('asymmetric filter') showed a higher leukocyte removal capacity than membranes of uniform pore size. However, only a 25% leukocyte removal was obtained with this 'asymmetric' filter, which contained a series of 8 membranes (FIG. 8). The filtration method described in the above application is therefore not useful for the purpose of leukocyte removal from blood products.

Other recent patents have described the use of polyvinylidene fluoride and polyvinyl formal membranes for use in leukocyte removal (see e.g. WO 89/02304).

Leukocyte removal by commercial nitrocellulose membranes has been described in U.S. Pat. Nos. 5,820,755 and 5,707,526 (Kraus et al.). A leukocyte removal of 97–99% was obtained using filters including nitrocellulose membranes in a main filter layer, and an upstream pre-filter as illustrated in FIG. 1. However, since the membrane is more efficient in leukocyte capture than the pre-filter media, the leukocytes form a concentrated "cake" in the membrane layer and further filtration causes some of the leukocytes to leak out as illustrated in the figure. Such leakage may make filtration quality unacceptable.

SUMMARY OF THE INVENTION

There is provided in accordance with one embodiment of the invention a filter unit for a blood-derived suspension containing leukocytes, the filter unit comprising: a main filter for blocking the leukocytes comprising at least one membrane layer, and a post-filter for preventing leakage of the leukocytes comprising at least one layer wherein the post-filter is placed downstream of said main filter and has a median pore size higher than the median pore size of said main-filter.

Further in accordance with an embodiment of the invention the main filter comprises at least one nitrocellulose membrane layer or nylon membrane layer which may be modified by a surface treatment reaction and has a median pore size in the range of 5–15 microns.

Further in accordance with an embodiment of the invention the post-filter comprises at least one non-woven polymer fabric layer and/or membrane layer.

Further in accordance with an embodiment of the invention the filter unit comprising at least one pre-filter placed upstream of the main filter and having a median pore size higher than the median pore size of the main filter.

There is thus provided in accordance with an embodiment of the invention a method for removing leukocytes from a blood-derived suspension comprising leukocytes, comprising the step of: passing the suspension through a filter unit including main-filter for blocking leukocytes and post-filter located downstream of the main-filter.

BRIEF DESCRIPTION OF THE DRAWING

The invention will be understood and appreciated more fully from the following detailed description taken in conjunction with the appended drawings.

DETAILED DESCRIPTION OF THE INVENTION

In the following description, various aspects of the invention will be described. For purposes of explanation, specific configurations and details are set forth in order to provide a thorough understanding of the invention. However, it will also be apparent to one skilled in the art that the invention may be practiced without the specific details presented herein. Furthermore, well known features may be omitted or simplified in order not to obscure the invention.

Embodiments of the invention provide a filter unit and a method for removing leukocytes from leukocyte-containing suspensions.

In one embodiment the filter unit construction has a filter for removing leukocytes from a leukocyte-containing suspension. Such a filter unit can be constructed, for example, from a conventional reusable filter holder. Two or more layers are placed in the filter holder, which is tightly closed and connected to a reservoir containing blood or blood product. The blood or blood product is then allowed to flow gravitationally through the filter unit. The layers can be easily replaced after one or more blood units have been filtered through them. Alternatively, the filter unit can be constructed from a disposable filter housing into which the layers are heat-sealed, glued or clamped mechanically.

Various leukocyte-containing suspensions can be filtered using embodiments of the invention. These include, for example, whole blood, packed red blood cells, platelet concentrate etc.

Figure 1:
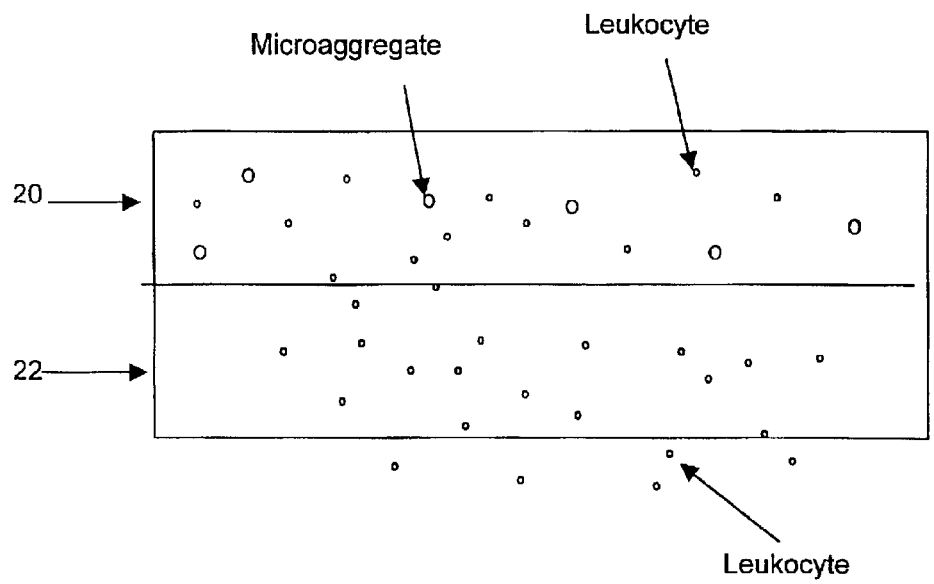
FIG. 1 is a schematic illustration of a leukocyte filter according to the prior art.
Figure 2:
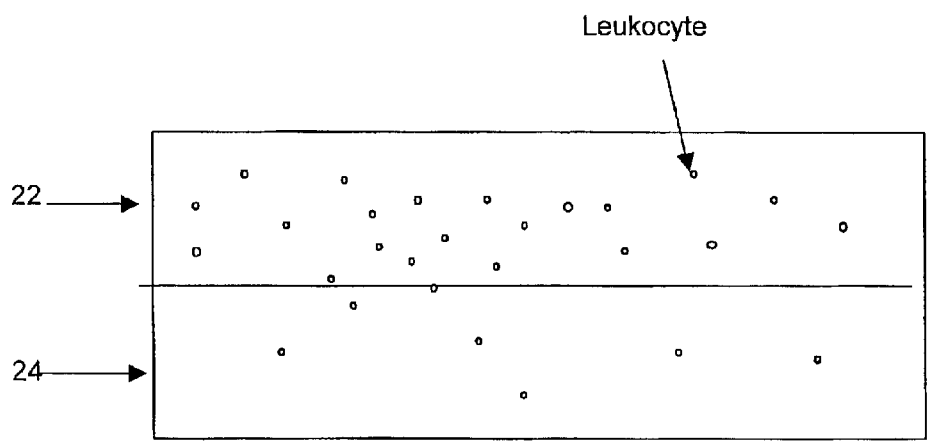
FIG. 2 is a schematic illustration of a filter unit constructed of a main filter and a downstream filter according to one embodiment of the invention.

Reference is now made to FIG. 2, which illustrates a filter unit 10 including a main filter 22 and a post-filter 24 according to one embodiment of the invention. "Post-filter" is defined herein as a filter that is placed downstream of a main filter.

In one embodiment the main filter 22 comprises at least one membrane, having a median pore size ranging from 5–15 $\mu$m, preferably 8–12 $\mu$m, and more preferably 8–10 $\mu$m. The membrane may be a cellulose membrane, for example, nitrocellulose membrane or non-cellulose membrane, for example, nylon membrane. Other pore sizes and other types or constructions of membranes may be used.

Nitrocellulose membranes which have been modified may be used in embodiment of the invention. This modification may be accomplished by, for example, performing a surface treatment reaction in which the membrane is exposed to a suitable initiator while in contact with a monomer. The initiator may be chemical, or it may be gamma or U.V. radiation. Suitable monomers can be various acrylic monomers carrying functional groups such as hydroxy, carboxy or others.

In one embodiment a post-filter 24 comprising at least one filter layer is placed downstream of the main filter. The post-filter 24 may comprise a membrane such as nitrocellulose or nylon membrane, a non-woven filter or other structures and material filters. The non-woven filter may be prepared for example, from polymer fibers such as polyesters, polyurethane, polypropylene etc. The post filter has a median pore size greater than the median pore size of the main filter. The non-woven filter having a median pore size preferably ranging from 5 to 30 $\mu$m and larger than the median pore size of the main filter. Other pore sizes may be used.

In operation, typically a blood suspension containing leukocytes 30 is passed and gravitationally filtered through filter unit 10.

It has been found, and shown in the following examples, that post-filter layer arrangements can substantially affect leukocyte filter performance. Whereas in the prior art, pre-filter layers were placed exclusively upstream of the main filter layers, it was found that placing post-filters downstream of the main filter layers can significantly improve filter performance. Thus, even when using the same total filter mass, moving some of the pre-filter layers downstream improves leukocyte retention.

Without limiting the invention in any way, the filtration improvement achieved by the post-filter may be explained by the following: In filters, especially those based on membranes as a main filter media, the membranes are much more efficient in leukocyte capture than the pre-filter media. Consequently, the leukocytes form a highly concentrated "cake" in the membrane layer. Further filtration causes some of the captured leukocytes to leak out. Such leakage, even if constituting only a small percentage of the total leukocyte mass, may make filtration quality unacceptable.

A common solution for such leukocyte leakage is to add an additional main filter layer, or use a tighter main filter media. This however, adversely affects cost and flow rate. The addition of more upstream pre-filter layers has little effect since the highly concentrated cake would still form and leak.

A novel solution for such leukocyte leakage, according to embodiments of the invention, is the placement of a post-filter downstream of the cake-containing membrane layers. This post-filter can be an additional layer, or preferably existing layers moved from an upstream position to a downstream position. Such a post-filter has sufficient mass and thickness to capture the small leak downstream of the main media. The economic cost for applying the novel arrangement is nil or low since when using an existing layer only the layers arrangement is different and no addition of layers is required.

Figure 3:
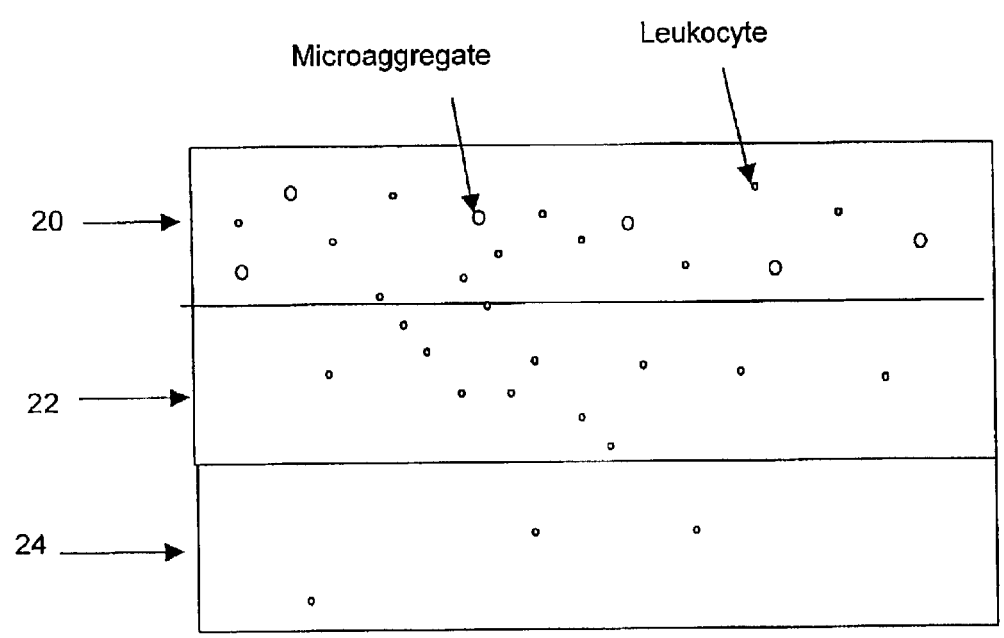
FIG. 3 is a schematic illustration of a filter unit constructed of an upstream pre-filter, main filter and a downstream filter according to another embodiment of the invention.

Reference in now made to FIG. 3, which illustrates a filter unit 10 including an upstream pre-filter 20, a main filter 22 and a downstream filter 24 according to another embodiment of the invention.

The upstream pre-filter 20 typically comprises a non-woven filter that may be prepared from polymer fibers such as polyesters, polyurethane, polypropylene, etc. The pre-filter may be constructed from any other material and may have other pore sizes or structures. The upstream pre-filter 20 is placed upstream of the main filter 22 and the post-filter 24. The upstream pre-filter may be constructed from the same material as post filter 24 or from a different material. The upstream filter acts to remove larger particles and some of the leukocytes, thus reducing the load on the main filter. A blood suspension containing leukocytes 30 is passed and gravitationally filtered through filter unit 10.

The following examples further illustrate and describe the invention disclosed herein. The invention is not to be limited in scope by the following examples.

In the examples the following legends will be used:

US: upstream side $NC(M)_X$: nitrocellulose membrane of the main filter $Nylon(M)_X$: nylon membrane of the main filter $NC(Pr)_X$: nitrocellulose membrane of the pre filter $NC(Pt)_X$: nitrocellulose membrane of the post filter $Nylon(Pr)_X$: nylon membrane of the pre filter $Nylon(Pt)_X$: nylon membrane of the post filter $NW(Pr)_X$: non-woven of the pre filter $NW(Pt)_X$: non-woven of the post filter X: number of layers The results of each example are summarized in a table showing the incoming and filtrate leukocyte count and the filtrate platelets and Red Blood Cell (RBC) percent. Each of the examples below of embodiments of the invention may be modified and may include other components, arrangements and structures.

EXAMPLE 1

Comparison Between Cellolose Based Three Component Leukocyte Reduction Filter and Cellulose Based Two Component Filter Both the three component leukocyte reduction filter and the two component filters were made of nitrocellulose membrane layers and non-woven layers. All layers were treated to prevent platelet adhesion. One unit of blood was passed through the filters gravitationally.

| Filter arrangement | | Incoming leukocyte count | Total filtrate leukocyte count | Filtrate Platelets percent | Filtrate RBC percent |
|---|---|---|---|---|---|
| Three component filter | US NW(Pr)$_9$/NC(M)$_5$/NW(Pt)$_9$/NC(Pt)$_5$ | 6400/$\mu$l | 0.85 × 10$^6$ | 84% | 92% |
| Two component filter (prior art) | US NW(Pr)$_{18}$/NC(M)$_{10}$ | 6400/$\mu$l | 4–6 × 10$^6$ | 85% | 92% |

In this example, the three component filter is comprised of non-woven pre-filter, nitrocellulose main filter and a combination of nitrocellulose and non-woven post filter. In this example, the two component filter comprises non-woven pre-filter and nitrocellulose main filter. As shown in the table the three component filter arrangement has a clear advantage in leukocyte removal efficiency when compared to a two component filter arrangement.

EXAMPLE 2

Comparison Between Cellulose Based Three Component Leukocyte Reduction Filter With Reduced Membrane Layer Number, and Two Component Filter A reduced scale filter similar to the filter in Example 1 was built and compared to a two component filter as in Example 1. Both filters were made of nitrocellulose membrane layers and non-woven layers. All layers were treated to prevent platelet adhesion. One unit of blood was passed through the filters gravitationally.

| Filter arrangement | | Incoming leukocyte count | Total filtrate leukocyte count | Filtrate Platelets percent |
|---|---|---|---|---|
| Three component filter | US NW(Pr)$_{18}$/NC(M)$_4$/NW(Pt)$_6$/NC(Pt)$_1$ | 5000/$\mu$l | 0.7 × 10$^6$ | 67% |
| Two component filter (prior art) | US NW(Pr)$_{18}$/NC(M)$_{10}$ | 5000/$\mu$l | 1.4 × 10$^6$ | 70% |

In this example, the three component filter is comprised of a non-woven pre-filter, a nitrocellulose main filter and a combination of nitrocellulose and non-woven post filter. In this example, the two component filter comprises a non-woven pre-filter and nitrocellulose main filter. As shown in the table the three component filter arrangement has an advantage over the two component filter in leukocyte removal efficiency, even with the reduced number of nitrocellulose membrane layers.

EXAMPLE 3

Comparison Between Cellulose Based Three Component Leukocyte Reduction Filter for Whole Blood, and Two Component Filter A filter similar to the filter in Example 1 was assembled, except that the layers were not chemically treated. Therefore platelets contained in a blood unit were adsorbed in addition to the leukocytes. Both filters were made of nitrocellulose membrane layers and non-woven layers. Whole blood was passed through the filters gravitationally.

| Filter arrangement | | Incoming leukocyte count | Total filtrate leukocyte count | Filtrate Platelets percent | Filtrate RBC percent |
|---|---|---|---|---|---|
| Three component filter | US NW(Pr)$_9$/NC(M)$_4$/NW(Pt)$_8$/NC(Pr)$_2$/NW(Pt)$_9$ | 6700/$\mu$l | 0.1 × 10$^5$ | 0% | 90% |
| Two component filter (prior art) | US NW(Pr)$_{18}$/NC(M)$_{10}$ | 6400/$\mu$l | 3 × 10$^5$ | 1% | 92% |

In this example, the three component filter is comprised of a non-woven pre-filter, a nitrocellulose main filter and a combination of non-woven, nitrocellulose and non-woven post filter. In this example, the two component filter comprises a non-woven pre-filter and nitrocellulose main filter. As shown in the table the three component filter arrangement has an advantage over the two component filter in leukocyte removal efficiency, at a substantially lower membrane mass.

EXAMPLE 4

Comparison Between Nylon Based Three Component Leukocyte Reduction Filter and Two Component Filter Both the three component leukocyte filter and the two component filter were made of nylon membrane layers (MSI—Osmonics 20 micron) and non-woven layers. All layers were treated to prevent platelet adhesion. One unit of blood was passed through the filters gravitationally.

|  | Filter arrangement | Incoming leukocyte count | Total filtrate leukocyte count | Filtrate Platelets Percent | Filtrate RBC percent |
|---|---|---|---|---|---|
| Three component filter | US NW(Pr)$_5$/Nylon(M)$_1$/ NW(Pt)$_5$ | 5400/$\mu$l | 1.8 × 10$^6$ | 71% | 90% |
| Two component filter (prior art) | US NW(Pr)$_{10}$/Nylon(M)$_1$ | 5400/$\mu$l | 4 × 10$^6$ | 71% | 92% |

In this example, the three component filter is comprised of a non-woven pre-filter, a nylon main filter and a non-woven post filter. In this example, the two component filter comprises a non-woven pre-filter and nylon main filter. As shown in the table the three component filter arrangement has a clear advantage in leukocyte removal efficiency when compared to a two component filter arrangement.

EXAMPLE 5

Comparison Between Mixed Cellulose/Nylon Based Three Component Leukocyte Reduction Filter and Two Component Filter Both the three component leukocyte filter and the two component filter were made of nitrocellulose membrane layers, nylon membrane layers (MSI—Osmonics 20 micron) and non-woven layers. All layers were treated to prevent platelet adhesion. One unit of blood was passed through the filters gravitationally.

|  | Filter arrangement | Incoming leukocyte count | Total filtrate leukocyte count | Filtrate Platelets percent | Filtrate RBC Percent |
|---|---|---|---|---|---|
| Three component filter | US NW(Pr)$_{24}$/NC(M)$_2$/ Nylon(M)$_1$/NW(Pt)$_2$ | 5400/$\mu$l | 0.7 × 10$^6$ | 80% | 90% |
| Two component filter (prior art) | US NW(Pr)$_{26}$/NC(M)$_2$/ Nylon(M)$_1$ | 5400/$\mu$l | 2.7 × 10$^6$ | 68% | 92% |

In this example, the three component filter is comprised of a non-woven pre-filter, a combination of nitrocellulose and nylon main filter and a non-woven post filter. In this example the two component filter is comprised of a non-woven pre-filter and a combination of nitrocellulose and nylon main filter. As shown in the table the three component filter arrangement has a clear advantage in leukocyte removal efficiency when compared to a two component filter arrangement including an upstream pre-filter and a main filter.

What is claimed is:

1. A filter unit comprising:
   a main filter for blocking leukocytes, said main filter comprising at least one membrane layer; and
   a post-filter for preventing leakage of said leukocytes, placed downstream of said main filter having a median pore size higher than the median pore size of said main-filter.

2. A filter twit according to claim 1 wherein said main filter has a median pore size in the range of 5–15 microns.

3. A filter unit according to claim 1 wherein said main filter comprises at least one nitrocellulose membrane layer.

4. A filter unit according to claim 1 wherein said main filter comprises at least one nylon membrane layer.

5. A filter unit according to claim 1, wherein said main filter comprises a membrane which is modified by a surface treatment reaction.

6. A filter unit according to claim 1, wherein said post-filter comprises at least one non-woven polymer fabric layer.

7. A filter unit according to claim 1, wherein said post-filter comprises at least one membrane layer.

8. A filter unit according to claim 7, wherein said membrane is a nitrocellulose membrane.

9. A filter unit according to claim 7, wherein said membrane is a nylon membrane.

10. A filter unit according to claim 1, wherein said post-filter comprises a plurality of layers comprising at least one membrane layer and at least one non-woven polymer fabric layer.

11. A filter unit according to claim 1 comprising at least one pre-filter, said pre-filter placed upstream of said main filter and having a median pore size higher than the median pore size of said main filter.

12. A filter unit comprising:
 a main filter for blocking leukocytes. said main filter comprising at least one membrane layer; and
 a post-filter for preventing leakage of said leukocytes, said post-filter comprising at least two layers of non-woven polymer wherein said post-filter is placed downstream of said main filter and has a median pore size higher than the median pore size of said main-filter.

13. A filter unit comprising:
 a pre-filter;
 a main filter for blocking leukocytes, comprising at least one membrane layer; and
 a post-filter for preventing leakage of said leukocytes, placed downstream of said main filter and has a median pore size higher than the median pore size of said main-filter.

14. A method for removing leukocytes comprising the step of:
 passing a leukocyte containing suspension through a filter unit including a main-filter for blocking leukocytes, comprising at least one membrane layer, and a post-filter for preventing leakage of said leukocytes, located downstream of said main-filter, wherein the median pore size of said post-filter is higher than the median pore size of said main-filter.

15. The method of claim 14, wherein said suspension is gravitationally passed through said filter.

16. The method of claim 14, wherein said filter unit farther comprises a pre-filter located upstream of said main filter and having a median pore size higher than the median pore size of the main filter.

17. The method of claim 14, wherein said main filter has a median pore size in the range of 5–15 microns.

18. The method of claim 14, wherein said main filter comprises at least one nitrocellulose membrane layer.

19. The method of claim 14, wherein said main filter comprises at least one nylon membrane layer.

20. The method of claim 14, wherein said main filter comprises a membrane which is modified by a surface treatment reaction.

21. The method of claim 14, wherein said post-filter comprises at least one non-woven polymer fabric layer.

22. The method of claim 14, wherein said post-filter comprises at least one membrane layer.

23. The method of claim 22, wherein said membrane is a nitrocellulose membrane.

24. The method of claim 22, wherein said membrane is a nylon membrane.

25. The method of claim 14, wherein said post-filter comprises a plurality of layers comprising at least one membrane layer and at least one non-woven polymer fabric layer.

* * * * *